United States Patent [19]

Vargas

[11] Plant 5,248

[45] Jun. 19, 1984

[54] ROSE PLANT—JACJEM

[75] Inventor: Jose E. Vargas, Wasco, Calif.

[73] Assignee: Jackson & Perkins Company, Medford, Oreg.

[21] Appl. No.: 448,921

[22] Filed: Dec. 13, 1982

[51] Int. Cl.[3] ..... A01H 5/00

[52] U.S. Cl. ..... Plt./3

[58] Field of Search ..... Plt./3

*Primary Examiner*—Robert E. Bagwill

*Attorney, Agent, or Firm*—Klarquist, Sparkman, Campbell, Leigh & Whinston

[57] ABSTRACT

A climber rose variety, being substantially identical to its parent variety, Jacjem, but distinguished therefrom by long canes attaining mature height of at least ten feet.

1 Drawing Figure

1

The present invention relates to a new and distinct variety of rose plant of the climber class, which was discovered by me as a sport of the variety Jacjem, seedling number 74-2681, U.S. application Ser. No. 299,024 (now U.S. Plant Pat. No. 5,001).

At the time of my discovery aforementioned, I was in charge of the growing of a large block of plants of the bush rose variety, Jacjem being grown in fields at Wasco, Calif.

In the course of one of my inspections of these fields, my attention was attracted to one plant on which appeared a climbing branch. Upon close examination of this plant, I found that it had sported and I thereupon promptly took steps to preserve the sport, keep it under observation, and to asexually reproduce the same by budding, as performed at Wasco, Calif., for the purpose of determining whether its climbing habit was fixed and transmissible by asexual reproduction. The climbing habit was fully confirmed and transmitted through several propagations.

The accompanying illustration shows a typical specimen of my new variety showing the climbing habit of growth, the colors of various vegetative parts being as nearly true as it is reasonably possible to make the same in a color illustration of this character.

2

The parent variety Jacjem is a popular rose variety of the bush type, floribunda class, but so far as I am aware, it has never previously exhibited a climbing habit and its growth has been that of the average bush rose.

The new variety is substantially identical in all respects to its parent, except that it is definitely a climber, as evidenced by its long, strong canes which attain a mature length of at least ten feet or more. In view of the general similarities between the new sport variety and its parent, except as noted in the foregoing, it is unnecessary specifically to describe the new variety in detail herein, since it otherwise substantially conforms to the detailed description embodied in plant patent application Ser. No. 299,024, (now U.S. Plant Pat. No. 5,001).

I claim:

1. A new and distinct variety of rose plant of the climber class, substantially as herein shown and described, characterized particularly as to novelty by being substantially identical with its parent variety, Jacjem, U.S. plant patent application Ser. No. 299,024 (now U.S. Plant Pat. No. 5,001), in almost every respect, but being distinguished therefrom by its long, strong canes which attain a mature height of at least ten feet or more, indicative of its climbing habit of growth.

* * * * *

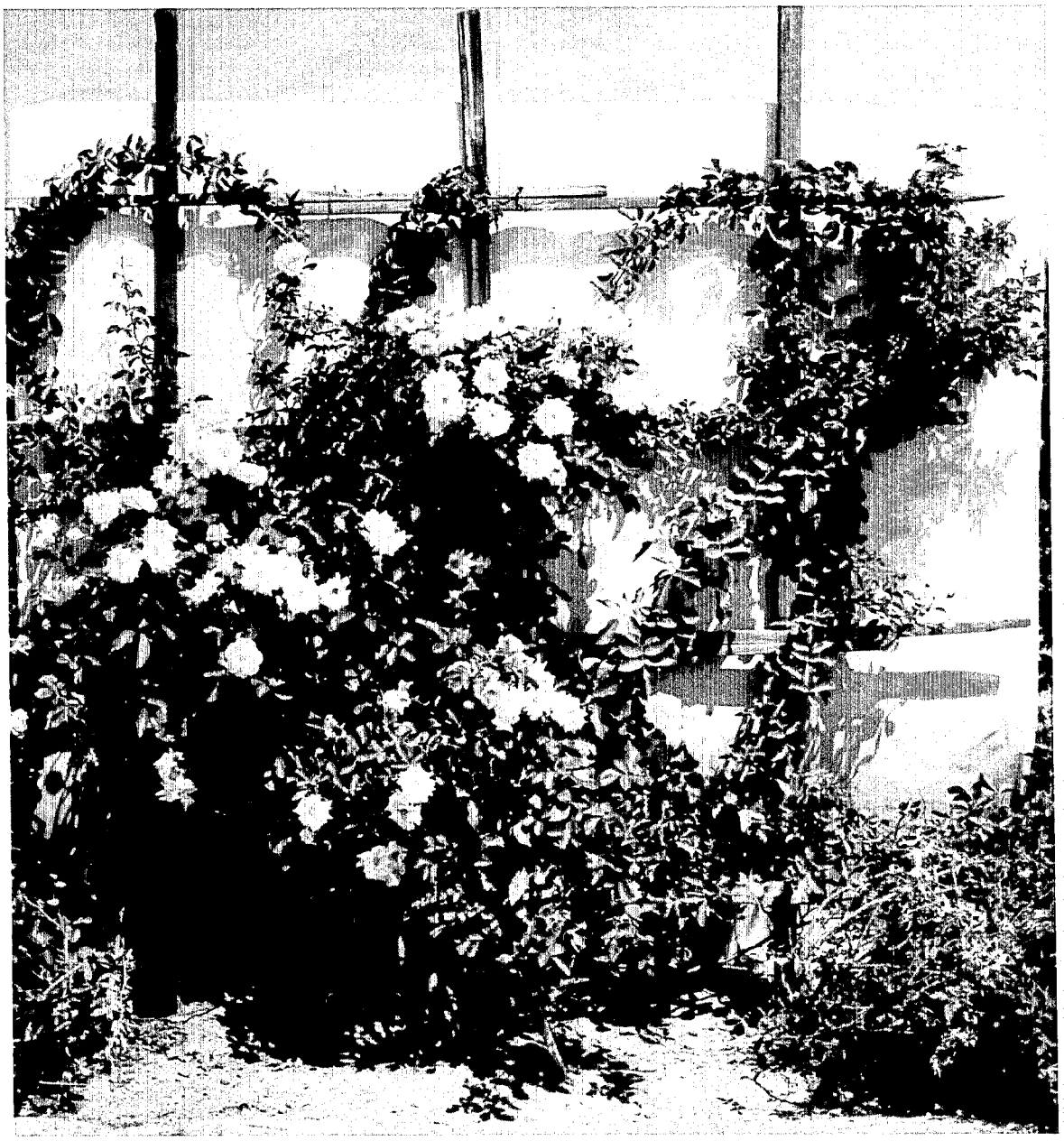

UNITED STATES PATENT AND TRADEMARK OFFICE

CERTIFICATE OF CORRECTION

PATENT NO. : Plant Patent No. 5248

DATED : June 19, 1984

INVENTOR(S) : Jose E. Vargas

It is certified that error appears in the above-identified patent and that said Letters Patent is hereby corrected as shown below:

The title of the patent should be changed from "ROSE PLANT - JACJEM" to --ROSE PLANT - JACLEM--.

Signed and Sealed this

*Twenty-sixth* Day of *March 1985*

[SEAL]

*Attest:*

DONALD J. QUIGG

*Attesting Officer* *Acting Commissioner of Patents and Trademarks*